United States Patent [19]

Georgiev et al.

[11] Patent Number: 4,749,793

[45] Date of Patent: Jun. 7, 1988

[54] 5-SUBSTITUTED-3-PHENYL-3-[1H-IMIDAZOL-1-YLMETHYL) OR (1H-1,2,4-TRIAZOL-1-YLMETHYL]-2-BENZYLISOXAZOLIDINES (IR 3011)

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,747

[22] Filed: Oct. 2, 1987

[51] Int. Cl.$^4$ .................. A61K 31/41; C07D 261/00
[52] U.S. Cl. .................. 548/240; 548/242; 548/262
[58] Field of Search .............. 548/240, 242, 262; 514/378

[56] References Cited

U.S. PATENT DOCUMENTS

| | | | |
|---|---|---|---|
| 3,415,978 | 10/1975 | Kulsa | 548/240 |
| 3,709,901 | 1/1973 | Draber | 548/235 |
| 3,711,495 | 1/1973 | Kulsa | 548/242 |
| 3,987,179 | 10/1976 | Nadelson | 548/243 |
| 4,010,176 | 3/1977 | Kulsa | 548/242 |
| 4,510,154 | 4/1985 | Yoshida | 514/365 |

FOREIGN PATENT DOCUMENTS 171137  2/1986  European Pat. Off. ............ 548/215
7956726 6/1979  Japan.

OTHER PUBLICATIONS

Boyce, C. B. (1977) Chem. Abstract 87:23258a.
Funaki, Y. (1980) Chem. Abstract 92:128915u.
Kelly, R. C. (1980) Chem. Abstract 93:114498u.
Haken, P. T. (1980) Chem. Abstract 93:132471i.
Sokolov, S. V. (1961) Chem. Abstract 55:7399.
Kano, H. (1965) Chem Abstract 62:9139d.
Kano, H. (1965) Chem. Abstract 63:8367a.
Takahi, Y. (1974) Chem. Abstract 81:22233c.

Primary Examiner—Donald G. Daus
Assistant Examiner—Mark W. Noel

[57] ABSTRACT

5-Substituted-3-phenyl-3-[1H-imidazol-1-ylmethyl) or (1H-1,2,4-triazol-1-ylmethyl)]-2-benzylisoxazolidines are useful as antifungal agents.

6 Claims, No Drawings

5-SUBSTITUTED-3-PHENYL-3-[1H-IMIDAZOL-1-YLMETHYL) OR (1H-1,2,4-TRIAZOL-1-YLMETHYL]-2-BENZYLISOXAZOLIDINES (IR 3011)

BACKGROUND OF THE INVENTION

This invention pertains generally to substituted 2-methylisoxazolidines and more specifically to 5-substituted-3-phenyl-3-[(1H-imidazol-1-ylmethyl) or (1H-1,2,4-triazol-1-ylmethyl)]-2-benzylisoxazolidines which are useful as antifungal agents.

BRIEF SUMMARY OF THE INVENTION

In accordance with this invention there are provided compounds of the formula:

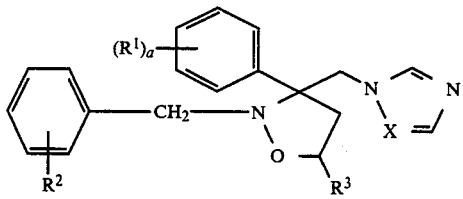

and the pharmaceutically acceptable acid addition salts thereof, in the form of their enantiomers or mixtures of their enantiomers including diastereomeric pairs of such enantiomers, wherein;
- a = 1 or 2,
- $R^1$ is selected from hydrogen, halogen, lower alkyl, lower alkoxy groups, and combinations thereof, provided that the ortho position is hydrogen,
- $R^2$ is selected from hydrogen, and one or more halogen, lower alkyl and lower alkoxy groups and combinations thereof,
- $R^3$ is selected from phenyl, substituted phenyl, styryl, substituted styryl, substituted phenoxymethyl and substituted phenylthiomethyl groups wherein the substituents at the phenyl rings are selected from one or more halogen, lower alkoxy and lower alkyl groups and combinations thereof, and
- X is selected from CH or N.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, New York, N.Y. (1980)]. The compound prepared in Example 3 was found to have good to moderate inhibitory activity against a broad spectrum of organisms including *Trichophyton mentagrophytes, Trichophyton rubrum, Trichophyton schoenleinii, Epidermophyton floccosum* and *Candida stellatoidea* with a minimum inhibitory concentration, MIC, of 2 to 20 µg/ml.

Because of their antifungal activity, the compounds of the invention can be used, for example, in suitable liquid, semisolid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

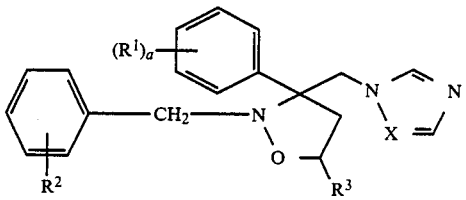

and the pharmaceutically acceptable acid addition salts thereof, in the form of their enantiomers or mixtures of their enantiomers including diastereomeric pairs of such enantiomers, wherein;
- a = 1 or 2,
- $R^1$ is selected from hydrogen, halogen, lower alkyl, lower alkoxy groups and combinations thereof, provided that the ortho position is hydrogen,
- $R^2$ is selected from hydrogen, and one or more (preferably one or two) halogen, lower alkoxy and lower alkyl groups and combinations thereof,
- $R^3$ is selected from phenyl, substituted phenyl, styryl, substituted styryl, substituted phenoxymethyl and substituted phenylthiomethyl groups wherein the phenyl rings can be substituted with one or more (preferably one or two halogen, lower alkoxy and lower alkyl groups and combinations thereof, and
- X is selected from CH and N.

By halogen is meant chlorine, bromine, fluorine and iodine with chlorine and fluorine being preferred. By lower alkyl is meant alkyl groups containing one to four (1-4) carbons. By lower alkoxy is meant such groups containing one to six (1-6) carbons. Alkyl groups with three or more carbons can have a branched or unbranched chain.

The 5-substituted-3-phenyl-3-(1H-imidazol-1-ylmethyl)-2-benzylisoxazolidine derivatives of the invention are obtained as a mixture of cis- and trans-diastereomers due to the presence of two asymmetric carbon atoms in the isoxazolidine ring. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The eluents may be used alone on in combinations such as the ones comprised of 95–99% halogenated hydrocarbon and 1–5% alkanol by volume. The stereochemistry of the two asymmetric carbon atoms in the isoxazolidine ring may be determined by conventional methods that include x-ray crystallography, nuclear magnetic resonance spectroscopy, circular dichroism and optical rotatory dispersion. Both the cis- and trans-diastereoisomers are resolvable into their optical enantiomers with (+)- and (−)-optical rotations by standard techniques such as fractional recrystallization of the diastereomeric salts with optically active organic acids such (+)- and (−)-tartaric acid, (+)- and (−)-dibenzoyltartaric acid and the like.

The compounds of the invention can be prepared as illustrated in the following diagram. The synthesis of the nitrone precursors 3 is accomplished by reacting an appropriately substituted 2-imidazolylacetophenone 1 with substituted N-benzylhydroxylamine 2 as described in our copending application Ser. No. 900,856 filed Aug. 27, 1986 whose disclosure is incorporated herein by reference. Subsequent reaction of the nitrone 3 with an appropriate 1-alkene derivative 4 provides a diastereomeric mixture of the desired cis- and trans-5-substituted-3-phenyl-3-(1H-imidazol-1-ylmethyl)-2-benzylisoxazolidine derivative 5.

(c) N-[(4-Methoxyphenyl)methyl]hydroxylamine (2, $R^2$=4-OCH$_3$), m.p. 65°–70° C. (ethyl acetate/hexane, 1:1 by volume).

EXAMPLE 1

3-(4-Fluorophenyl)-3-(1H-imidazol-1-ylmethyl)-5-phenyl-2-(phenylmethyl)isoxazolidine (5, $R^1$=4-F, $R^2$=H, $R^3$=C$_6$H$_5$)

A suspension of 2.00 g (0.0098 mol) of 1-(4-fluorophenyl)-2-(1H-imidazol-1-yl)ethanone (1, $R^1$=4-F), 1.30 g (0.011 mol) of N-(phenylmethyl)hydroxylamine (2, $R^2$=H), 0.82 g (0.010 mol) of sodium acetate, and

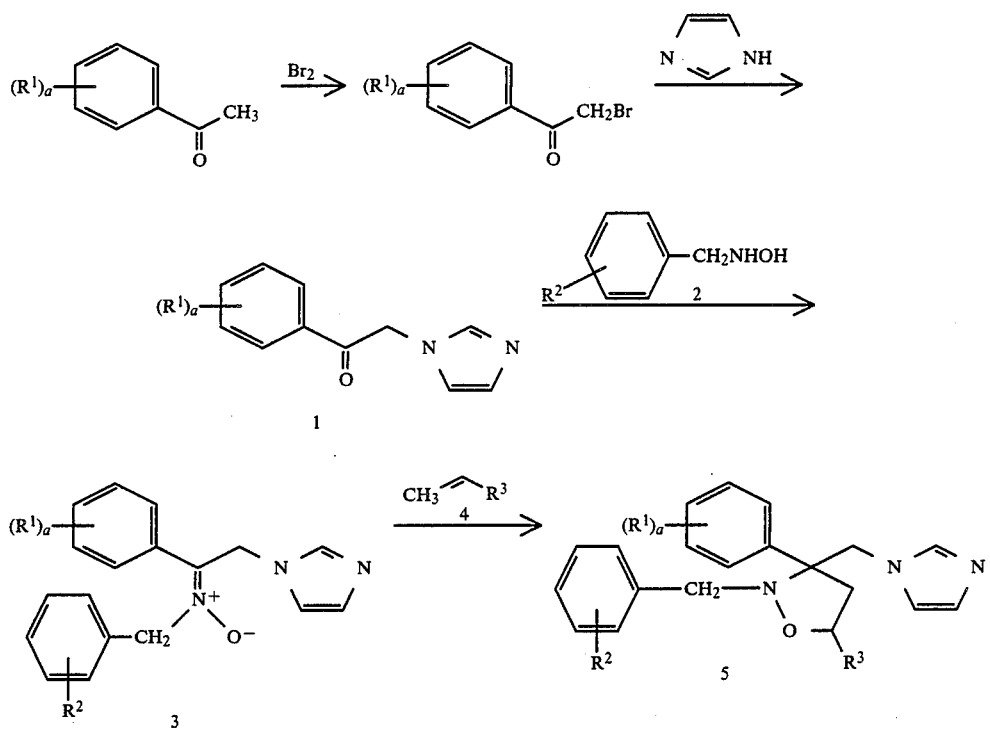

Scheme

Similarly by using 2-(1H-1,2,4,-triazol-1-yl)acetophenone, the corresponding 3-(1H-1,2,4-triazol-1-ylmethyl)isoxazolidine can be prepared.

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

PREPARATION OF INTERMEDIATES

The hydroxylamines 2 were prepared from their corresponding oximes by the method of Kawase and Kikugawa [J. Chem. Soc., Perkin I, 643–645 (1979)]:

(a) N-[(3-Chlorophenyl)methyl]hydroxylamine hydrochloride (2, $R^2$=3-Cl), m.p. 161°–169° C. (ethanol), (b) N-[(4-Fluorophenyl)methyl]hydroxylamine hydrochloride (2, $R^2$=4-F), m.p. 70°–76° C. (ether), 0.60 ml (0.010 mol) of acetic acid in 25 ml of ethanol is heated to reflux under a nitrogen atmosphere and stirred for 24 hours. Upon cooling to ambient temperature, the suspension is poured into 50 ml of water, neutralized with sodium bicarbonate and extracted with chloroform (2×50 ml). The combined organic extract is dried over anhydrous magnesium sulfate, concentrated in vacuo, and flash-chromatographed on neutral silica gel using a 9:1 by volume mixture of ethyl acetate and methanol as the eluent, to give 1.63 g (54%) of 1-(4-fluorophenyl)-2-(1H-imidazol-1-yl)-N-(phenylmethyl)ethanimine N-oxide (3, $R^1$=4-F, $R^2$=H) as a light yellow oil. This oil (0.0053 mol) is dissolved in 50 ml of toluene, 1.5 ml (0.013 mol) of styrene (4, $R^3$=C$_6$H$_5$) is added, and the solution is refluxed under a nitrogen atmosphere for 28 hours, cooled to ambient temperature and concentrated in vacuo. The resulting cis- and trans-diastereomeric mixture of compound 5 ($R^1$=4-F, $R^2$=H, $R^3$=C$_6$H$_5$) is flash-chromatographed on neutral silica gel using a 98.2 by volume mixture of chloroform and methanol as the eluent.

Isomer A (0.98 g, 45%) has a melting point of 162°–164° C. (ethyl acetate). Anal. Calcd. for $C_{26}H_{24}FN_3O$: C, 75.52; H, 5.85; F, 4.59; N, 10.16. Found: C, 75.50; H, 6.04; F, 4.74; N, 10.05.

EXAMPLE 2

3-(4-Chlorophenyl)-3-(1H-imidazol-1-ylmethyl)-2-[(4-methoxyphenyl)methyl]-5-phenylisoxazolidine (5, $R^1$=4-Cl, $R^2$=4-OCH$_3$, $R^3$=C$_6$H$_5$)

Compound 5 ($R^1$=4-Cl, $R^2$=4-OCH$_3$, $R^3$=C$_6$H$_5$) is prepared by a method similar to that described in Example 1 by reacting 8.06 g (0.0365 mol) of 1-(4-chlorophenyl)-2-(1H-imidazol-1-yl)ethanone (1, $R^1$=4-Cl) with 8.39 g (0.055 mol) of N-[(4-methoxyphenyl)methyl]hydroxylamine (2, $R^2$=4-OCH$_3$) to give 4.42 g (34%) of 1-(4-chlorophenyl)-2-(1H-imidazol-1-yl)-N-[(4-methoxyphenyl)methyl]ethanimine N-oxide (3, $R^1$=4-Cl, $R^2$=4-OCH$_3$) as a light yellow oil, followed by reaction of 3 ($R^1$=4-Cl, $R^2$=4-OCH$_3$) (4.42 g, 0.0124 mol) with 1.90 g (0.018 mol) of styrene (4, $R^3$=C$_6$H$_5$). The resulting cis- and trans-diastereomeric mixture of compound 5 ($R^1$=4-Cl, $R^2$=4-OCH$_3$, $R^3$=C$_6$H$_5$) is flash-chromatographed on neutral silica gel using a 95:5 by volume mixture of ethyl acetate and methanol (saturated with ammonia) as the eluent.

Isomer A (2.61 g, 46%) has a melting point of 162°–167° C. (ethyl acetate-hexane, 1:1 by volume). Anal. Calcd. for $C_{27}H_{26}ClN_3O_2$: C, 70.50; H, 5.70; Cl, 7.71; N, 9.14. Found: C, 70.40; H, 5.80; Cl, 8.13; N, 9.14.

EXAMPLE 3

5-[(4-Chlorophenoxy)methyl]-3-(1H-imidazol-1-ylmethyl)-3-phenyl-2-(phenylmethyl)isoxazolidine (5, $R^1$=$R^2$=H, $R^3$=CH$_2$OC$_6$H$_4$Cl-4)

Compound 5 ($R^1$=$R^2$=H, $R^3$=CH$_2$OC$_6$H$_4$Cl-4) is prepared by a method similar to that described in Example 1 by reacting 3.72 g (0.020 mol) of 2-(1H-imidazol-1-yl)-1-phenylethanone (1, $R^1$=H) with 2.95 g (0.024 mol) of N-(phenylmethyl)hydroxylamine (2, $R^2$=H) to give 2-(1H-imidazol-1-yl)-1-phenyl-N-(phenylmethyl)ethanimine N-oxide (3, $R^1$=$R^2$=H), followed by reaction of 3 ($R^1$=$R^2$=H) with 3.59 g (0.021 mol) of allyl 4-chlorophenyl ether (3, $R^3$=CH$_2$OC$_6$H$_4$Cl-4). The resulting cis- and trans-diastereomeric mixture of compound 5 ($R^1$=$R^2$=H, $R^3$=CH$_2$OC$_6$H$_4$Cl-4) is flash-chromatographed on neutral silica gel using a 98:2 by volume mixture of chloroform and methanol as the eluent.

Isomer A (2.55 g, 27.7% overall) has a melting point of 128°–130° C. (ethyl acetate-hexane, 1:1). Anal. Calcd. for $C_{27}H_{26}ClN_3O_2$: C, 70.50; H, 5.70; Cl, 7.71; N, 9.14. Found: C, 70.48; H, 5.82; Cl, 7.85; N, 9.06.

Isomer B (0.040 g, 4.3% overall) has a melting point of 110°–113° C. (ethyl acetate-hexane, 1:1). Anal. Calcd. for $C_{27}H_{26}ClN_3O_2$: C, 70.50; H, 5.70; Cl, 7.71; N, 9.14. Found: C, 70.16; H, 5.56; Cl, 7.88; N, 9.12.

EXAMPLE 4

5-[(4-Chlorophenoxy)methyl]-2-[(3-chlorophenyl)methyl]-3-(1H-imidazol-1-yl-methyl)-3-phenylisoxazolidine (5, $R^1$=H, $R^2$=3-Cl, $R^3$=CH$_2$OC$_6$H$_4$Cl-4)

Compound 5 ($R^1$=H, $R^2$=3-Cl, $R^3$=CH$_2$OC$_6$H$_4$Cl-4) is prepared by a method similar to that described in Example 1 by reacting 5.20 g (0.028 mol) of 2-(1H-imidazol-1-yl)-1-phenylethanone (1, $R^1$=H) with 8.20 g (0.042 mol) of N-[(3-chlorophenyl)methyl]hydroxylamine hydrochloride (2, $R^2$=3-Cl) to give 5.39 g (59%) of N-[(3-chlorophenyl)methyl]-2-(1H-imidazol-1-yl)-1-phenylethanimine N-oxide (3, $R^1$=H, $R^2$=3-Cl), followed by reaction of 3 ($R^1$=H, $R^2$=3-Cl) (5.39 g, 0.0165 mol) with 4.20 g (0.0248 mol) of allyl 4-chlorophenyl ether (4, $R^3$=CH$_2$OC$_6$H$_4$Cl-4). The resulting cis- and trans-diastereomeric mixture of compound 5 ($R^1$=H, $R^2$=3-Cl, $R^3$=CH$_2$OC$_6$H$_4$Cl-4) is flash-chromatographed on neutral silica gel using a 98:2 by volume mixture of chloroform and methanol as the eluent.

Isomer A (2.0 g, 2.45%) has a melting point of 103°–107° C. (ethyl acetate-hexane, 1:1). Anal. Calcd. for $C_{27}H_{25}ClN_3O_2$: C, 65.59; H, 5.10; Cl, 14.34; N, 8.50. Found: C, 65.47; H, 5.15; Cl, 14.50; N, 8.48.

EXAMPLE 5

2-[(4-Fluorophenyl)methyl]-3-(1H-imidazol-1-ylmethyl)-5-[[(4-methylphenyl)thio]methyl]-3-phenylisoxazolidine (5, $R^1$=H, $R^2$=4-F, $R^3$=CH$_2$SC$_6$H$_4$CH$_3$-4)

Compound 5 ($R^1$=H, $R^2$=4-F, $R^3$=CH$_2$SC$_6$H$_4$CH$_3$-4) is prepared by a method similar to that described in Example 1 by reacting 3.20 g (0.0173 mol) of 2-(1H-imidazol-1-yl)-1-phenylethanone (1, $R^1$=H) with 3.66 g (0.0259 mol) of N-[(4-fluorophenyl)methyl]hydroxylamine (2, $R^2$=4-F) to give 2.44 g (45.6%) of N-[(4-fluorophenyl)methyl]-2-(1H-imidazol-1-yl)-1-phenylethanimine N-oxide (3, $R^1$=H, $R^2$=4-F), followed by reaction of 3 ($R^1$=H, $R^2$=4-F) (1.49 g, 0.0048 mol) with 1.20 g (0.007 mol) of allyl 4-methylphenyl sulfide (4, $R^3$=CH$_2$SC$_6$H$_4$CH$_3$-4). The resulting cis- and trans-diastereomeric mixture of compound 5 ($R^1$=H, $R^2$=4-F, $R^3$=CH$_2$SC$_6$H$_4$CH$_3$-4) is flash-chromatographed on neutral silica gel using a 98:2 by volume mixture of chloroform and methanol as the eluent.

Isomer A (1.26 g, 55%) has a melting point of 168°–172° C. (ethyl acetate) as its monohydrochloride salt. Anal. Calcd. for $C_{28}H_{29}ClFN_3OS$: C, 65.93; H, 5.73; Cl, 6.95; F, 3.72; N, 8.24; S, 6.29. Found: C, 65.59; H, 5.88; Cl, 7.37; F, 3.64; N, 8.09; S, 6.62.

EXAMPLE 6

5-Substituted-3-(phenyl or substituted phenyl)-3-(1H-1,2,4-triazol-1-ylmethyl)-2-(benzyl or substituted benzyl)isoxazolidines (X=N)

By following essentially the same methods as described for Examples 1–5 and replacing 1-(phenyl or substituted phenyl)-2-(1H-imidazol-1-yl)-N-[(phenyl or substituted phenyl)methyl]ethanimine N-oxide by, 1-(phenyl or substituted phenyl)-2-(1H-1,2,4-triazol-1-yl)-N-[(phenyl or substituted phenyl)methyl]ethanimine N-oxide, the corresponding 5-substituted-3-(phenyl or substituted phenyl)-3-(1H-1,2,4-triazol-1-ylmethyl)-2-(benzyl or substituted benzyl)isoxazolidines can be prepared. For example, 3-(4-fluorophenyl)-3-(1H-1,2,4-triazol-1-ylmethyl)-5-phenyl-2-(phenylmethyl)isoxazolidine, 3-(4-chlorophenyl)-3-(1H-1,2,4-triazol-1-ylmethyl)-2-[(4-methoxyphenyl)methyl]-5-phenylisoxazolidine, 5-[(4-chlorophenoxy)methyl]-3-(1H-1,2,4-triazol-1-ylmethyl)-3-phenyl-2-(phenylmethyl)isoxazolidine, 5-[(4-chlorophenoxy)methyl]-2-[(3-chlorophenyl)methyl]-3-(1H-1,2,4-triazol-1-ylmethyl)-3-phenylisoxazolidine, 2-[(4-fluorophenyl)methyl]-3-(1H-1,2,4-triazol-1-ylmethyl)-5-{[(4-methylphenyl)thio]methyl}-3-phenylisoxazolidine, 3-(4-methoxyphenyl)-3-(1H-1,2,4-triazol-1-ylmethyl)-5-phenyl-2-[(4-methylphenyl)methyl]isoxazolidine, 3-(4-chloro-3-methylphenyl)-3-(1H-1,2,4-triazol-1-ylmethyl)-5-(4-methoxyphenyl)-2-[(4-chloro-3-methylphenyl)methyl]isoxazolidine, 3-(4-fluorophenyl)-3-(1H-1,2,4-triazol-1-ylmethyl)-5-(2-trans-phenylethenyl)-2-[(4-methylphenyl)methyl]isoxazolidine, and 3-(4-methylphenyl)-3-(1H-1,2,4-triazol-1-ylmethyl)-5-phenyl-2-[(3-chlorophenyl)methyl]isoxazolidine.

Salts of the compounds of the invention can be prepared as known in the art, for example, by dissolving the compound in a 10:1 by volume mixture of ethanol and aqueous acid such as HCl or HNO₃, evaporating the solvent, and then recrystallizing the crude salt, for example, from methanol-ether, 1:3 by volume in the case of HCl salts, and ethanol in the case of HNO₃ salts.

We claim:

1. A compound of the formula:

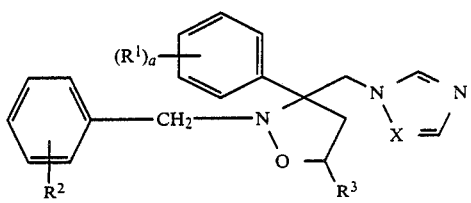

and the pharmaceutically acceptable acid addition salts thereof, in the form of their enantiomers or mixtures of their enantiomers including diastereomeric pairs of such enantiomers, wherein;

a=1 or 2, $R^1$ is selected from hydrogen, halogen, lower alkyl, lower alkoxy groups, and combinations thereof, provided that the ortho position is hydrogen, $R^2$ is selected from hydrogen, and one or more halogen, lower alkyl and lower alkoxy groups and combinations thereof, $R^3$ is selected from phenyl, substituted phenyl, styryl, substituted styryl, substituted phenoxymethyl and substituted phenylthiomethyl groups wherein the substituents at the phenyl rings are selected from one or more halogen, lower alkoxy and lower alkyl groups and combinations thereof, and X is selected from CH or N.

2. The compound of claim 1 wherein the compound is 3-(4-fluorophenyl)-3-(1H-imidazol-1-ylmethyl)-5-phenyl-2-(phenylmethyl)isoxazolidine.

3. The compound of claim 1 wherein the compound is 3-(4-chlorophenyl)-3-(1H-imidazol-1-ylmethyl)-2-[(4-methoxyphenyl)methyl]-5-phenylisoxazolidine.

4. The compound of claim 1 wherein the compound is 5-[(4-chlorophenoxy)methyl]-3-(1H-imidazol-1-ylmethyl)-3-phenyl-2-(phenylmethyl)isoxazolidine.

5. The compound of claim 1 wherein the compound is 5-[(4-chlorophenoxy)methyl]-2-[(3-chlorophenyl)methyl]-3-(1H-imidazol-1-ylmethyl)-3-phenylisoxazolidine.

6. The compound of claim 1 wherein the compound is 2-[(4-fluorophenyl)methyl]-3-(1H-imidazol-1-ylmethyl)-5-[[(4-methylphenyl)thio]methyl]-3-phenylisoxazolidine.

* * * * *